США Patent [19]

Hoerenz et al.

[11] Patent Number: 4,657,013
[45] Date of Patent: Apr. 14, 1987

[54] ILLUMINANCE DOSAGE DEVICE FOR AN OPERATION MICROSCOPE

[75] Inventors: Peter G. Hoerenz, Hartsdale, N.Y.; Gerhard Mueller, Aalen, Fed. Rep. of Germany

[73] Assignee: Carl-Zeiss-Stiftung, Heidenheim/Brenz, Fed. Rep. of Germany

[21] Appl. No.: 715,408

[22] Filed: Mar. 25, 1985

[51] Int. Cl.$^4$ ............................................. A61B 17/36
[52] U.S. Cl. .............................. 128/303.1; 356/215; 356/226; 350/507; 350/523
[58] Field of Search ............... 356/215, 218, 226, 227; 250/205; 350/507, 523, 524, 525, 526, 527; 128/303.1, 395–398, 664–667

[56] References Cited

U.S. PATENT DOCUMENTS

| | | | |
|---|---|---|---|
| 3,617,137 | 11/1971 | Meyers | 356/215 |
| 3,703,176 | 11/1972 | Vassiliadis et al. | 128/395 |
| 4,055,768 | 10/1977 | Bromberg | 356/317 |

*Primary Examiner*—Kyle L. Howell
*Assistant Examiner*—Randy Citrin

*Attorney, Agent, or Firm*—Hopgood, Calimafde, Kalil, Blaustein & Judlowe

[57] ABSTRACT

The invention contemplates dose-integrating instrumentation which relies upon continuously monitoring the illuminance level of a small sampling fraction of the total projected-light flux of the field-illuminating system of an operating microscope, the sampling being optionally within the projection system, or taken elsewhere. The sampled illuminance is in the form of an electrical signal which is continuously time-integrated to provide a continuous display of the dosage as it builds in the course of an operative procedure. Provision is made for the surgeon to preset what he chooses to be the safe upper limit of integrated exposure, beyond which he does not wish to go for fear of possible jeopardy to the retina of his patient, and the instrument continuously indicates the remaining time for him to complete his operation, should he continue at the current level of illumination. The instrument also provides a succession of different indications throughout the progress of the operation, as successive predetermined thresholds of building dosage (exposure) are reached.

10 Claims, 9 Drawing Figures

ILLUMINANCE DOSAGE DEVICE FOR AN OPERATION MICROSCOPE

BACKGROUND OF THE INVENTION

The invention relates to operation microscopes, particularly for operations upon the eye, and to the control of field illumination for such operations.

In ophthalmic microsurgery, field illumination can damage the retina even though the focus of surgery is in a plane removed from the retina, for example an operation such as a radial keratotomy upon the cornea. It is, of course, the surgeon's responsibility to make sure that, even when performing a particular operation which does not involve the retina, he nevertheless avoids damaging exposure of the retina to his illumination. The problem is aggravated by the fact that illumination brightness will vary in the course of a particular procedure, in that bright illumination is only needed for short intervals, and there can be intervals of no illumination and/or reduced illumination. Retinal damage is a function of time integration of the different levels of illumination, over the full course of a given procedure; the damage becomes irreparable once a tolerance level of the integrated value has been exceeded. And the surgeon's skill, experience and intuition have had to be the basis for avoiding retinal damage, by executing operative steps with greatest efficiency and dispatch.

BRIEF STATEMENT OF THE INVENTION

It is an object of the invention to provide the ophthalmic surgeon with dosimeter instrumentation which can relieve him of major concern with the extent to which a light-sensitive organ such as the retina may have integrated its illumination exposure, in the course of a given operation.

It is a specific object to meet the above object with instrumentation which conservatively integrates illumination exposure of an eye during a given operative procedure on the eye.

Another specific object is to provide such instrumentation with means for preselecting a professionally determined conservative limit of illumination dosage for a given operative procedure on the eye, and to provide means whereby remaining exposure time at a given illumination level may be instantly available at all times throughout the operative procedure.

Another object is to achieve the above objects without impairing the surgeon's access for performance of his operative tasks.

The invention in a preferred embodiment achieves these objects and provides certain further features in instrumentation which relies upon continuously monitoring the illuminance level of a small sampling fraction of the total projected-light flux of the field-illuminating system of an operating microscope, the sampling being optionally within the projection system, or taken elsewhere. The sampled illuminance is in the form of an electrical signal which is continuously time-integrated to provide a continuous display of the dosage as it builds in the course of an operative procedure. Provision is made for the surgeon to preset what he chooses to be the safe upper limit of integrated exposure, beyond which he does not wish to go for fear of possible jeopardy to the retina of his patient, and the instrument continuously indicates the remaining time for him to complete his operation, should he continue at the current level of illumination. The instrument also provides a succession of different indications throughout the progress of the operation, as successive predetermined thresholds of building dosage (exposure) are reached.

DETAILED DESCRIPTION

An illustrative embodiment of the invention will be described in detail, in conjunction with the accompanying drawings, in which.

Figure 1:
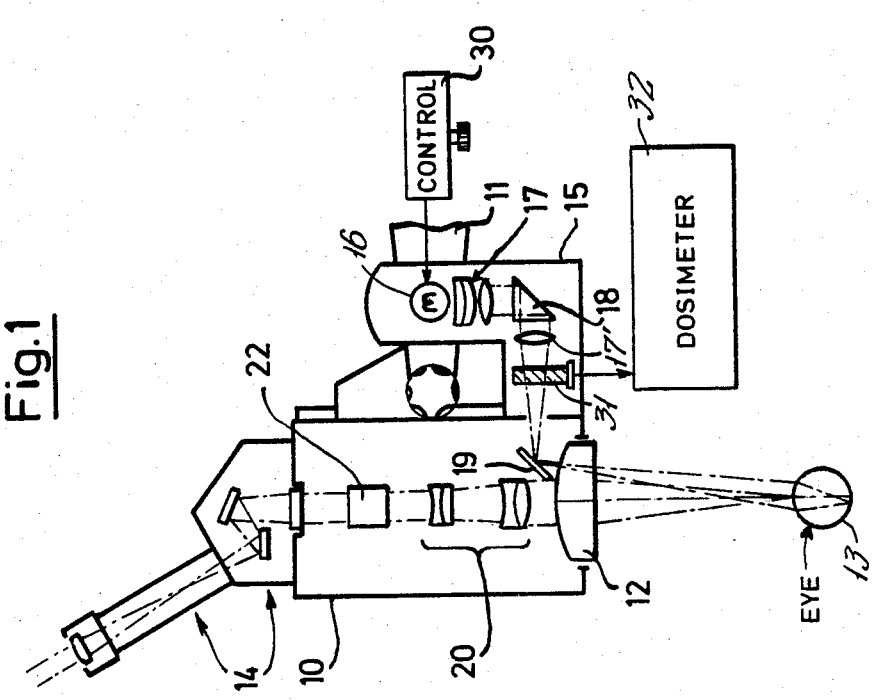
FIG. 1 is a simplified optical diagram of a binocular operation microscope embodying a dosimeter instrument of the invention, in the context of an eye to be operated upon, the aspect of the diagram being a side elevation.
Figure 2:
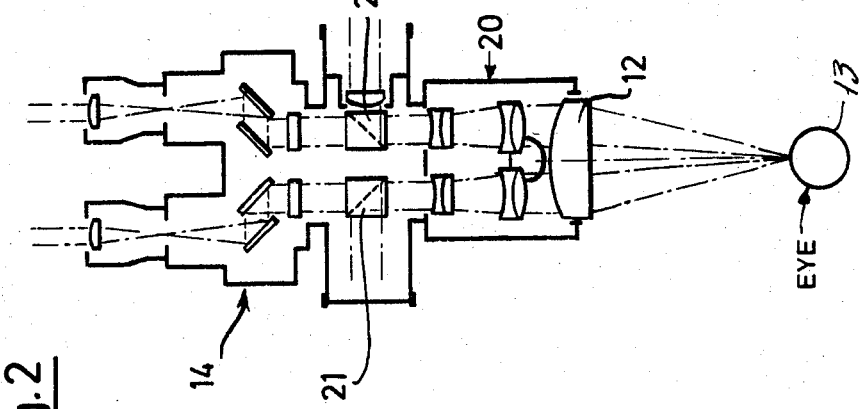
FIG. 2 is a similar diagram for the front elevation.

In FIGS. 1 and 2, the invention is shown in application to a binocular operation microscope wherein a housing 10 is adapted for mounting to a support arm 11 and carries a single main objective 12 serving spaced paths of stereoptical viewing alignments, from convergence at the cornea of an eye 13, to the respective halves of a binocular tube 14. Also using the same objective 12 is a field-illumination system within a side housing 15 and comprising a light source 16, a lens system 17-17', and a reflecting prism 18. Light thus cast by source 16 is reflected at 19 for traverse of objective 12 at an eccentrically offset location between the respective binocular-viewing paths; thus-projected light covers the object field at substantially the wide-angle limit of object viewing through the microscope.

In the collimated-light region between objective 12 and the ocular portion 14, the microscope may include one or more of various optical devices, such as a magnification changer 20, a beam splitter 21, as to serve a monocular-viewing tube, and a beam splitter 22 to serve a TV or photographic camera. The range of optical accessories optionally usable in this collimated-light region is of course more extensive, and the items mentioned are therefore to be understood as merely illustrative of auxiliary optical means which can have an attenuating or modulating effect upon instantaneous reflected-light flux arising from a given illumination of the object field and reaching the ocular region 14 of the microscope. These attenuating or modulating effects translate to the viewing surgeon as one of the needs to variously control the level of field illumination provided by light source 16, and a knob control for the purpose is indicated at 30.

Figure 5:
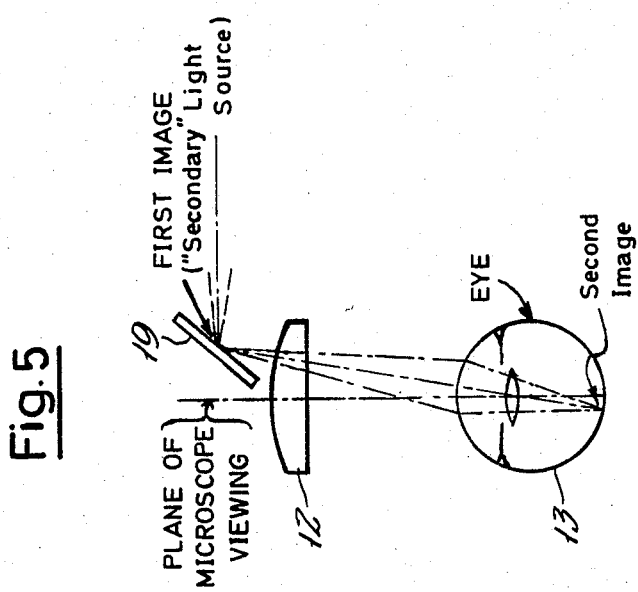
FIG. 5 is a simplified and fragmentary optical diagram from the aspect of FIG. 1, in aid of specific discussion

In accordance with the invention, the time-integration of a small fraction of the field-illumination flux, whatever the varying setting of control means 30, is taken as the measure of total dose exposure of the patient's retina in the course of a given operational procedure. In FIG. 1, this sampling occurs via a transparent flat plate 31 interposed between elements of the projection system and having sufficient internal scattering to permit generation of an electrical-signal output to a dosimeter instrument 32, the signal being illustratively generated by a photodetector, such as a silicon photodiode, edge-mounted to plate 31. The plate 31 may illustratively be of plexiglass, and it is shown positioned in a ray-convergence zone of the projection system, between lens element 17' and reflector 19. For the projection system shown, the filament of source 16 appears as a first image (or "secondary" light source, see FIG. 5) at the reflector 19, and light emerging from objective 12 is so projected that a second image can form at the retina of the eye being operated upon.

Figure 3:
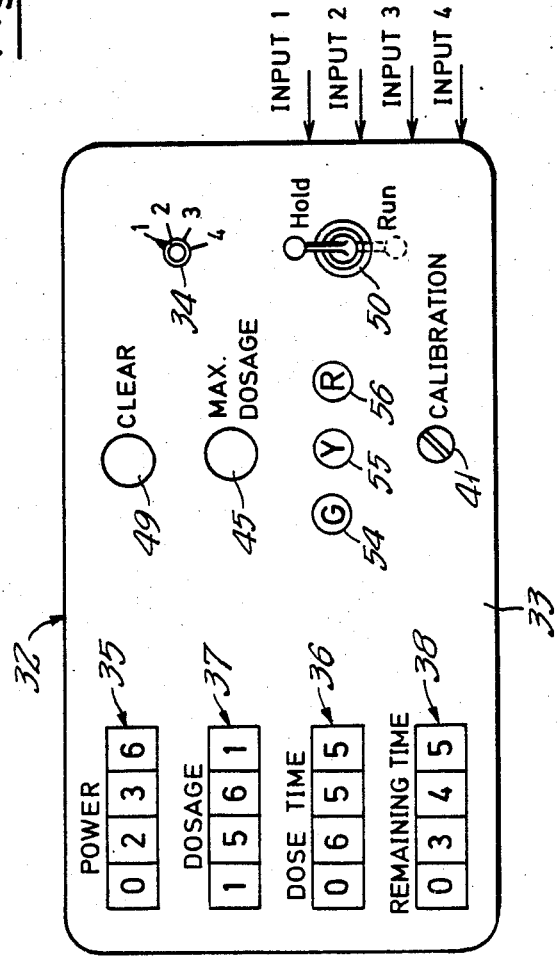
FIG. 3 is an enlarged view of the front panel of the dosimeter instrument of FIG. 1.
Figure 4:
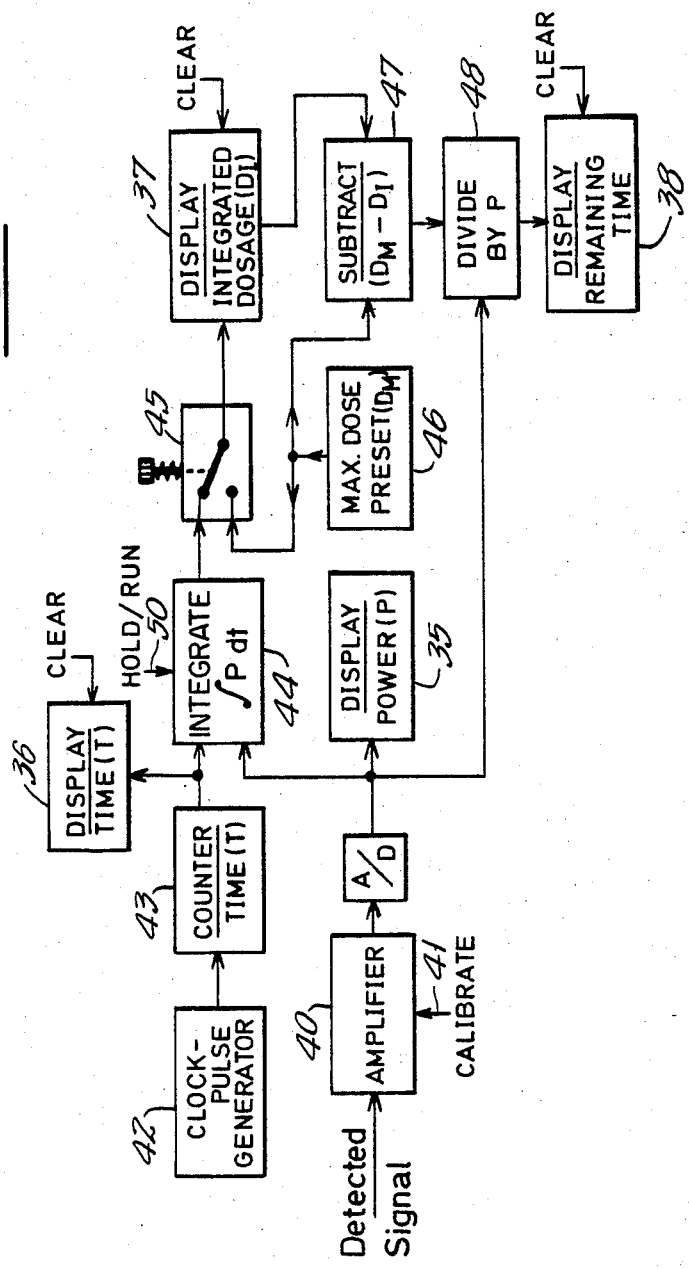
FIG. 4 is an electrical block diagram schematically indicating certain components of the dosimeter instrument.

Referring now to FIGS. 3 and 4, the front panel 33 of dosimeter 32 is seen to provide four separate decimal dose-related LED or liquid-crystal displays, applicable to any one of four optional input signals, as may be selected at 34; for the Input 1 that is shown to have been selected, the input signal will be in analog form, from the output of the edge-mounted sensor on plate 31. The display at 35 is labeled "POWER" and is a four-digit expression of the currently sensed intensity of the projection beam; the display at 36 is labeled "DOSE TIME" and is a four-digit expression of time lapse since commencement of the field-illuminating projected light; the display at 37 is labeled "DOSAGE" and is the instantaneous value of time-integrated intensity of the projected light; and the display at 38 is labeled "REMAINING TIME" and is the instantaneous value of time remaining to the point of reaching a preset upper limit of dosage, for the currently applicable level of projected illumination. Various other controls and indications at panel 33 will appear from description of the circuits of FIGS. 4 and 4a, FIG. 4 being relevant to generation of data presented at the displays 35-36-37-38.

In FIG. 4, legend indicates that the output of the light-sampling sensor is first supplied to an amplifier 40, having panel-mounted means 41 for calibrating adjustment. Amplifier output is processed for analog/digital conversion and is directly used for the POWER display 35, being symbolized P in FIG. 4. An independent self-contained generator 42 supplies clock pulses to a pulse counter 43, whereby to provide a digital output which is a strict measure of time (T) since commencement of projected-light exposure to the eye 13. An integrating circuit 44 accepts the digital output of the clock-pulse generator and of the detected-signal amplifier, effectively continuously multiplying the detected power (P) function by each unit of elapsed time (T). Circuit 44 may be a microprocessor connected and programmed to add an increment of integrated power, for each clock pulse (or predetermined submultiple thereof); and for the normal push-button switch connection shown at 45, the output of circuit 44 establishes the instantaneous integrated dose ($D_1$) display at 37; this display will advance at a faster rate, the greater the detected intensity of projected illumination.

To obtain data for the REMAINING TIME display at 38, the dosimeter includes means 46 for accepting the stored preset of a digital expression of maximum acceptable dosage ($D_M$). This may, for example, be set by push-button manipulation in the manner of presetting the alarm for a digital watch, the preset button (not shown) being preferably inaccessible via the panel 33, as by having it only accessible on a side or via the bottom of the dosimeter housing; by depressing the button of switch 45 while actuating the preset means 46, one has a display (at 38) of the instantaneous value of the preset maximum dose ($D_M$). Thus, with switch 45 in its normal position, the preset means 46 and the DOSAGE display 37 are sources of the respective maximum ($D_M$) and integrated ($D_I$) dose values, in digital form. The instantaneous value of their difference is continuously available from a circuit 47, and the digitally expressed difference is continuously supplied to a circuit 48, for continuous development of the quotient which results from division by the instantaneous digitally expressed power value P. The REMAINING TIME display 38 is established by this quotient.

All three of the displays at 36-37-38 are time-related, and legend indicates that they may all be cleared, for start of the next operational procedure. At panel 33, however, a single pushbutton actuator 49 will be understood to clear all three of these displays, for zero reset, at the same time.

At the integrating circuit 44, a manually selectable HOLD/RUN function is identified at 50. At panel 33, this switch 50 is shown in the HOLD position, meaning that the integrating function of circuit 44 is being temporarily discontinued, as by temporarily ceasing to supply further clock pulses while projected-light illumination is temporarily switched off. In its down or RUN position, switch 50 will be understood to enable circuit 44 to resume its continuous time-integration of the intensity (P) of field illumination.

Figure 4A:
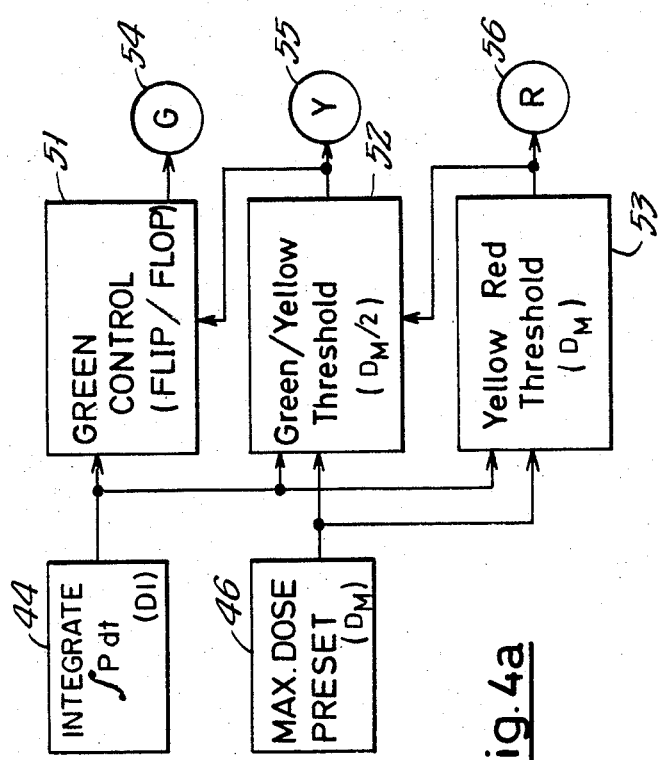
FIG. 4a is a similar schematic diagram for further components of the dosimeter.

The circuitry of FIG. 4a is illustrative of means further utilizing the digital dosage expressions $D_I$ and $D_M$, for simple colored-lamp indication of the dosage fraction with which a given instantaneous advance of operating exposure exists. A "green" or first-half-period signal (to illuminate a green lamp 54) may be provided by a flip/flop circuit 51 wherein the integrating circuit 44 is accumulating its tally of dosage ($D_I$) in an initial phase, say to the half-way value of the setting at 46 of maximum dosage. A first threshold circuit 52 may be set at the divide-by-two expression of the maximum dose ($D_M$), to provide a signal (to illuminate a yellow lamp 55 and to extinguish the green lamp 54 by changing the state of flip/flop 51) when the integrated value ($D_I$) reaches the $D_M/2$ threshold. And a second threshold circuit 53 may be set at the maximum level ($D_M$) to provide an output signal which illuminates a red lamp 56 (and extinguishes the yellow lamp 55) when the preset maximum-dose level is reached by the integrated dosage ($D_I$). This red signal is of course a real warning that further exposure of eye 13 to the projected illumination has now begun to exceed the conservative limit which the surgeon preset (at 46) as his maximum dosage.

Figure 6A:
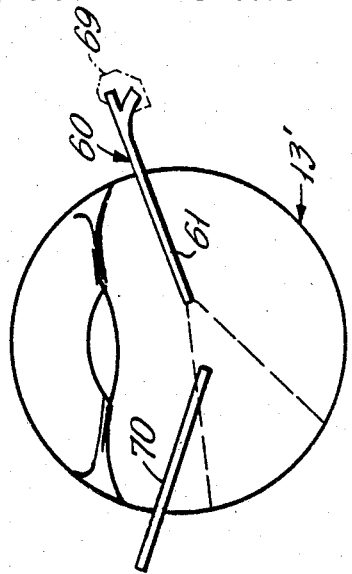
FIG. 6a is an enlarged and simplified diagram to illustrate use of the probe of FIG. 6.
Figure 6:
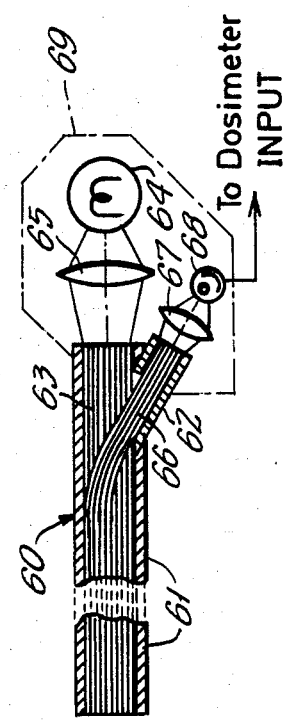
FIG. 6 is an enlarged, partly broken, longitudinal sectional view of an illumination probe alternatively usable with the dosimeter of the invention.

FIGS. 6 and 6a are illustrative of a probe 60 which provides both field illumination and a means of sampling a small fraction of the illumination for operation of the described dosimeter (FIGS. 3 and 4). Probe 60 is a small-diameter bundle of elongate optical fibers, within a suitable tubular enclosure 61 which has a smaller-diameter branch formation 62 at its axially outer end. Most of the optical fibers are straight, being identified 63 with outer ends directly exposed to light from a source 64, as focused by a lens 65. A small fraction 66 of the optical fibers extends continuously from within branch 62 to the distal end of the probe, for exposure to light reflected within an eye 13', a small surgical aperture in the wall of the eye having been made for entry of the probe into the posterior chamber of the eye. Light projected within the eye diverges as suggested by dashed lines, for manipulable illumination of selected areas of the posterior chamber; and a sampling of reflection of the projected light is available at the branch end for collection and focus by a lens 67 to a photocell 68, whereby the photocell (68) may provide a measured-luminance signal at, say, Input 2 to the dosimeter 32. The phantom outline 69 will be understood to indicate suitable miniaturized packaging of the source and sensing components 64–65 and 67–68 in unit-handling relation with the branched end of probe 60.

It will be understood that in the use situation depicted in FIG. 6a, manipulated position of and illumination by probe 60 within the posterior chamber of eye 13' may be monitored by the microscope of FIGS. 1 and 2, as may also the manipulated position and action of an elongate surgical tool 70, which is shown similarly introduced through the wall of the eye, via the side opposite entry by probe 60. And the arrangement of FIG. 6a will be understood to be illustratively applicable either to the suturing of an intraocular implant, or to the performance of vitreous surgery; the tool 70 may thus be a cutter/aspirator, or an infusor device. Further illustratively, the total number of fibers 63–66 in probe 60 may be 850, all contained within a 1-mm diameter bundle, and of these a small fraction, as for example a bundle of 50 fibers, taken preferably at random from the bundle of 850 fibers exposed at the distal end, may be diverted for reflected-light evaluation via the branch formation 62.

Figure 7:
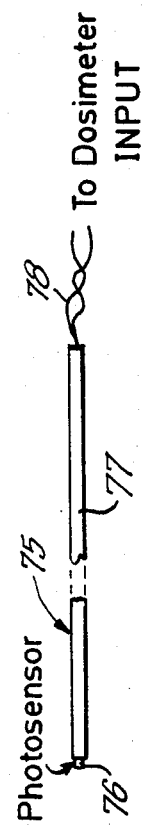
FIG. 7 is a simplified diagram of a photosensor probe optionally usable with the dosimeter of the invention.

The probe 75 of FIG. 7 is illustrative of a miniature photosensor 76 carried at the distal end of a small-diameter elongate rod 77 in which electrical output leads 78 are embedded, to enable external flexible connection to another of the selectively available inputs to dosimeter 32. Probe 75 may be used for measurement of illumination flux within the eye, as for an operative procedure within the anterior chamber to the eye, and when light from the projector source 16 is sufficient.

The described instrumentation will be seen to achieve all stated objects, providing a hitherto unavailable means whereby the surgeon can pace his operative procedure safely with the limiting dosage which he can preset from his own experience. The instrumentation enables the surgeon to establish (a) the irradiation level in the wound, (b) the duration of the operative intervention, (c) the dosage the operative field has received, and (d) operation time remaining at the current illumination level. The device can only objectively indicate irradiation levels and total dosage; it cannot make any conclusive decision about threshold values of dosage which may prove harmful to involved body tissue. For example, in ophthalmic microsurgery, the dosimeter 32 cannot assume the role of safeguard against retinal damage to the patient's eye, and it is the physician's responsibility to keep light levels and operation time strictly within safe limits which are based on his professional expertise; the indications at 35-36-37-38-54-55-56 only aid the physician, based on his own expert preset of a dosage limit at 46, and he can check this setting at any time, merely by pushing the button 45 and observing the numerical value then displayed at 37.

While the invention has been described in detail for a preferred embodiment, it will be understood that modification may be made without departure from the scope of the invention. For example, dosage measurement finds utility in operations other than when retinal protection is of concern.

What is claimed is:

1. In an operation microscope, comprising an objective and a viewing ocular at spaced locations along an optical-viewing path, and field-illumination means including a light source establishing an illuminating path via said objective to the viewing-path field of said objective, the improvement in which illumination-sampling means is positioned in said illuminating path, said sampling means including a detector producing an electrical-signal output responsive to a sampled fraction of illuminating flux at a location in the illuminating path, and field-dosage integrating means including a clock timer and connected for response to the output of said detector, said integrating means integrating detector output as a function of time of illumination on said illumination path, and said integrating means including display means for displaying the instantaneous integration value thereof.

2. The microscope of claim 1 in which said sampling means additionally comprises a substantially transparent plane-parallel plate having a degree of internal scattering, said detector being plate-mounted for edge response to internal scattering of illumination flux.

3. The microscope of claim 1 in which said sampling means comprises an elongate stem adapted at one end for surgical entry into the posterior chamber of an eye, and a photodetector at said end.

4. The microscope of claim 1, in which said sampling means comprises an elongate tubular container of a packed plurality of elongate optical fibers adapted at one end for surgical entry into the posterior chamber of an eye, with terminal ends of said fibers facing away from said one end, the other end of said container being characterized by a primary bundle of other terminal ends of the substantial majority of said fibers poised to receive incident illumination flux for fiber transmission to and discharge from said one end, and said container being further characterized by a secondary bundle of other terminal ends of a relatively small minority of said fibers, said secondary bundle being offset from said primary bundle at the respective other terminal ends of said bundles, and said detector having exposure to said secondary bundle at the other terminal end thereof.

5. The microscope of claim 1, in which said illumination-sampling means is interposed between said source and said objective.

6. The microscope of claim 1, in which said illumination-sampling means is in the viewing-path field of said objective.

7. In an operation microscope, comprising an objective and a viewing ocular at spaced locations along an optical-viewing path, and field-illumination means including a light source establishing an illuminating path via said objective to the viewing-path field of said objective, the improvement in which illumination-sampling means is positioned in said illuminating path, said sampling means including a detector producing an electrical-signal output responsvie to sampled fraction of illuminating flux at a location in the illuminating path, and field-dosage integrating means including a clock timer and connected for response to the output of said detector, said integrating means integrating detector output as a function of time of illumination on said illumination path, and presettable signal means for providing a predetermined reference signal value representing a predetermined maximum tolerable dosage level of said integration value, and indicator means responsive to said reference signal value and to the instantaneous integration value and producing an indicator signal upon attainment of an instantaneous integration value which is a predetermined fraction of said reference signal value.

8. The microscope of claim 7, in which said indicator means is further responsive to said refernece signal value and to the instantaneous integration value to produce a further indicator signal when said integration value attains said reference signal value.

9. In an operation microscope, comprising an objective and a viewing ocular at spaced locations along an optical-viewing path, and field-illumination means including a light source establishing an illuminating path via said objective to the viewing-path field of said objective, the improvement in which illumination-sampling means is positioned in said illuminating path, said sampling means including a detector producing an electrical-signal output responsive to a sampled fraction of illuminating flux at a location in the illuminating path, and field-dosage integrating means including a clock timer and connected for response to the output of said detector, said integrating means integrating detector output as a function of time of on said illumination path, and a presettable signal means for providing a predetermined reference signal value representing a predetermined maximum tolerable dosage level of said integration value, and indicator means differentially responsive to said reference signal value and to the instantaneous integration value to produce a difference signal value which is indicative of remaining tolerable dosage.

10. The microscope of claim 9, in which said indicator means includes an independent connection ot the detector output signal, and means for dividing said difference signal value by the detector output singal to thereby indicate remaining tolerable operating time at the currently sampled level of field illumination.

* * * * *